United States Patent [19]

Janata

[11] 4,151,049

[45] Apr. 24, 1979

[54] COMPOSITIONS HAVING PROTEIN REACTIVE GROUPS, MEMBRANES, ELECTRODES COATED WITH SUCH COMPOSITIONS AND CHEMICAL ANALYSIS METHODS

[75] Inventor: Jiri Janata, Salt Lake City, Utah

[73] Assignee: Imperial Chemical Industries Limited, London, England

[21] Appl. No.: 778,169

[22] Filed: Mar. 16, 1977

[30] Foreign Application Priority Data

Mar. 16, 1976 [GB] United Kingdom ............... 10465/76

[51] Int. Cl.$^2$ ..................... G01N 27/30; G01N 27/46; G01N/31/14
[52] U.S. Cl. ...................... 204/1 T; 195/63; 195/68; 195/103.5 R; 195/127; 195/DIG. 11; 204/195 M; 204/195 B; 204/296
[58] Field of Search ............. 204/195 M, 195 B, 1 E, 204/296; 427/307; 195/63, 68, DIG. 11, 103.5 R, 127; 260/6, 8

[56] References Cited

U.S. PATENT DOCUMENTS

| | | | |
|---|---|---|---|
| 3,966,580 | 6/1976 | Janata et al. | 294/195 B |
| 4,000,098 | 12/1976 | Hofstee | 195/127 X |

OTHER PUBLICATIONS

Peter D. G. Dean, Enzyme Technology Digest, vol. 3, No. 1, pp. 2-22, (1974).

*Primary Examiner*—G. L. Kaplan
*Attorney, Agent, or Firm*—Cushman, Darby & Cushman

[57] ABSTRACT

A specifically reactive polymeric composition comprising an organic hydrophobic polymeric substrate with a specific protein reactive group pendant therefrom is disclosed. The protein reactive group is a free group of a hydrocarbon chain which has one end thereof absorbed into the surface of said substrate, said protein reactive group being bound to said hydrocarbon chain via an ionic group. An electrode coated with a layer of the specifically reactive composition provides, in conjunction with a reference electrode, an electrically sensitive system for measuring change in concentration of a compound in solution where said compound reacts selectively with the composition.

7 Claims, No Drawings

COMPOSITIONS HAVING PROTEIN REACTIVE GROUPS, MEMBRANES, ELECTRODES COATED WITH SUCH COMPOSITIONS AND CHEMICAL ANALYSIS METHODS

This invention relates to organic compositions, and the preparation and use thereof, and to devices comprising such compositions.

German OLS No. DT 25 41 308 A1 describes a membrane comprising a hydrophobic polymer substrate having pendant from it essentially hydrocarbon chains carrying groups specifically reactive with a chemical compound, particularly a polypeptide. The aforementioned patent specification describes in particular the preparation of such a membrane by contacting a membrane having pendant hydrocarbon chains with a compound having appropriate reactive sites enabling it to bind the hydrocarbon to the specifically reactive group. Particularly exemplified therein is the use of a non-ionic material such as epichlorohydrin or a bis-epoxide as the binding compound.

The present invention provides a modification of the invention described in the aforementioned patent application in which, instead of a non-ionic compound we employ an ionic material to bind the specifically reactive group to the hydrocarbon chain.

Accordingly the present invention provides a specifically reactive composition comprising a hydrophobic organic polymeric substrate having pendant therefrom essentially hydrocarbon chains, said chains carrying groups specifically reactive with a chemical compound, and said groups being attached to the said hydrocarbon chains via an ionic grouping.

In a preferred composition according to the invention the linkage is an ionic protein binding linkage capable of binding a protein to the hydrocarbon chain of the composition. Any suitable ionic compound may be employed, the essential requirement being that it is capable of binding to at least a proportion of the pendant hydrocarbon chains of the composition and forming a linkage with the specifically reactive group and that where it forms a linkage with a protein it does not, under the conditions employed or to which the composition is exposed, cause undesirable denaturation of the protein.

Such materials have been described for example as mild cross-linking agents in protein chemistry (obviously most relevant when a protein component of the composition is contemplated.)

Our preferred ionic linkage is derived from an imido ester of the formula:

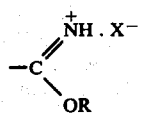

where R is an alkyl group, conveniently a lower alkyl, e.g. methyl or ethyl, and preferably methyl, and X is HCl or HBr, preferably HCl.

A hydrocarbon chain containing such a linkage may thus be represented as the imido ester thus:

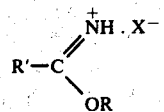

where R' is a hydrocarbon chain, which may be saturated or unsaturated, and which may be branched or straight. R' will usually contain from 6 to 20 carbon atoms, although it may contain more carbon atoms particularly if it is branched unsaturated. Preferably it will contain 8 to 14 carbon atoms. The hydrocarbon will usually be aliphatic.

Preferred is the methyl dodecyl imido ester.

The composition of the invention may find many applications where linkage of a grouping to a hydrophobic substrate is desired, for example in chromatography or selective reaction systems, and the compositions of the membranes of the aforementioned German OLS may find similar application also.

However, the composition finds use particularly in the form of a membrane which may be employed in association with a suitable electrical system, for example an electrode system, for analysis, detection or concentration determination. Thus in a preferred embodiment of the invention there is provided a hydrophobic membrane having protein immobilising ability, in association, e.g. encapsulating an electrode, conveniently a highly conductive electrode for example platinum. If a protein e.g. an antibody, having a selectivity for reaction with a particular protein (antigen) is reacted at the protein-reactive site, immersion of such a coated electrode in association with a reference electrode into an aqueous solution containing the antigen provides an electrically sensitive system capable of measuring the change in electrical charge of the solution-polymer interface caused by the capture of a particular protein (antigen) by the electrode with an immunoreactive antibody. Alternatively, an antigen may be immobilised on the membrane to selectively capture a corresponding antibody.

Thus, according to a further aspect of the invention there is provided an electrode encapsulated within a sheath of specifically reactive membrane as described above.

According to a further aspect of the invention there is provided a method of detecting the presence, and optimally the concentration, of a compound in a mixture containing the compound together with other molecules, e.g. solvent molecules, by contacting the mixture with an electrode encased within a membrane as described above specifically reactive with the compound, and detecting any resulting change in the electrical charge on the membrane. Conveniently this may be accomplished by comparison with an appropriate reference electrode.

EXEMPLARY PROCESS DESCRIPTION

A hydrophobic polymeric membrane having selective immunochemical ability (i.e. a specifically reactive membrane) is prepared by forming a membrane of a hydrophobic polymer. The polymer is preferably one which is capable of being swollen with an organic solvent, or mixture of solvents, particularly aliphatic solvents. Particularly useful polymers in the practice of this invention are those hydrophobic polymers which contain no pendant polar groups. Typical polymers for this purpose include thermoplastic polymers such as polyvinyl chloride, polystyrene, polyethylene, polypropylene, silicone rubber, polyurethane, polycarbonate, polytetrafluoroethylene and the like. Thermosetting polymers such as epoxy resins and crosslinked polyesters may also be used. Preferred polymers are those which may be coated upon an electrode by dip-casting or shrink-fitting.

The polymeric membrane is then treated with a solvent system capable of swelling the membrane for a period sufficient to result in swelling of the membrane at least to an extent that the hydrocarbon chain may be incorporated into the membrane in sufficient concentration, as subsequently described. The solvent system contains, besides an appropriate solvent, a hydrocarbon compound having a reactive site thereon, preferably at or near one end of the hydrocarbon chain. The solvents used to swell the polymeric membrane are preferably those which may be readily removed by drying of the polymer. Thus, lower molecular weight solvents are generally preferred to higher molecular weight solvents. As indicated hereinafter, it is preferred that the solvent is of a lower boiling point and more easily evaporated than the hydrocarbon compound having a reactive site thereon. A typical solvent mixture for PVC comprises petroleum ether of a 30° to 60° C. boiling range and toluene. Other solvents or mixtures thereof may be employed for the swelling of PVC or other polymeric materials, but these will be known to the skilled man or they may be determined by simple tests.

After the polymeric membrane has been soaked in the solvent system for a period sufficiently long to effect the required degree of swelling, the membrane is dried at an appropriate temperature to remove the solvent without removing substantial quantities of the hydrocarbon compound having the reactive site. When petroleum ether, toluene and solvents of similar boiling point range are utilised a typical drying temperature is about 50° to 100° C., conveniently 50° to 60° C., preferably under vacuum. Removal of the solvent gives a membrane having hydrocarbon chains pendant therefrom, each of said chains having a reactive group thereon. Selection of the solvent (and thereby its boiling point) and pressures to be employed in its removal will be made with regard to the nature and properties of membrane and of the hydrocarbon. The polymers used herein have known solvents for swelling same.

Following attachment of the hydrocarbon chain to the polymeric membrane a series of treatments may follow to provide a specifically reactive membrane, i.e., a membrane having the ability to capture a specific compound, for example a protein, an enzyme, or a mono- or poly-saccharide, as in an immunochemical reaction.

It will be appreciated that the hydrocarbon chain may be provided with the specific reactive group before its introduction into the membrane (in which case it will of course be necessary to ensure that the group is free to display its reactivity—preferably by ensuring that it is not located less than about 4–6 carbon atoms from the membrane), or the group may be introduced into the chain after its attachment to the membrane.

We prefer to provide the hydrocarbon chain with its protein reactive linkage before incorporation into the polymer and the incorporation of an imido ester into the polymer and subsequent contact with a proteinaceous specific reactive group may be represented schematically as follows:

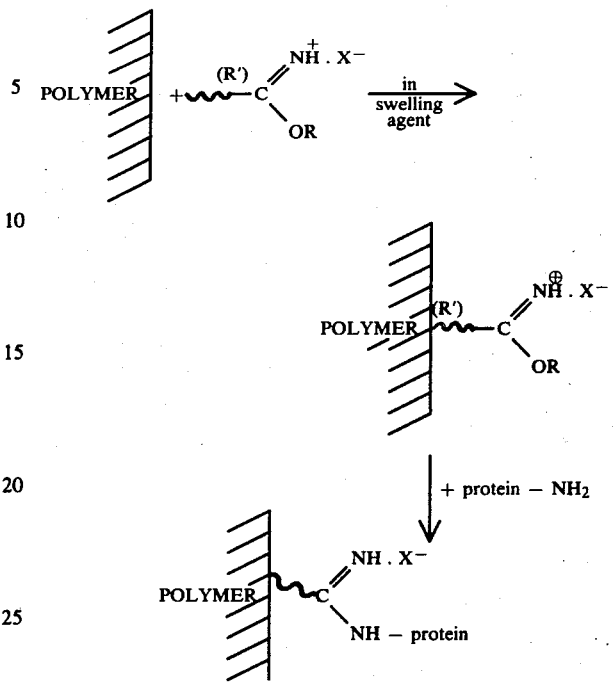

Where the hydrocarbon component is branched and of sufficient size incorporation into the polymer may occur at more than one location, i.e. two or more branches may form attachments to the polymer. When a branched hydrocarbon is employed branching will preferably occur at one or more carbon atom other than the α carbon so that the functioning of the ester link is not unduly interfered with.

It is desirable that there is no likelihood of cross-linking between a pair of pendant groups pending from the membrane surface.

After the protein-reactive linking compound (i.e. compound containing an immobilising group) is reacted with the chain pending from the membrane surface to produce the protein linking grouping, it is preferably washed and placed in a solution containing the protein to be immobilised. A preferred reaction temperature is room temperature and it is generally preferred to allow one or two days for the reaction to proceed. The reaction is generally conducted in a slightly basic medium.

After the protein is attached, it is treated to wash off residue of unreacted materials and further reacted with a compound to neutralise any unreacted protein-reactive, i.e. immobilising, groups which remained after reaction with the protein molecule.

In conducting the process according to the instant invention, it is generally preferred to use a hydrocarbon compound which has a sufficient chain length to permit the reactive group to be somewhat remote from the surface of the membrane. Generally the hydrocarbon compound employed according to the invention has at least six carbon atoms in the main chain length. A preferred length is one in which the main chain of the hydrocarbon compound contains about eight to fourteen carbon atoms, and in any case is preferably selected so that the specific reactive group is distant from the membrane surface by at least 4, and preferably at least 6 or even 8 carbon atoms. If a protein-reactive linking compound which is reacted therewith is of significant chain length, so that the ultimate protein-reactive group is pendant from the surface by at least six carbon atoms, then the chain length of the hydrocarbon need not be as long.

APPARATUS

The novel membranes of the instant invention are particularly useful inasmuch as they can be utilised in devices for detecting the presence of a particular compound qualitatively and, preferably, quantitatively in a given mixture e.g. solution containing the compound.

A sheath of the hydrophobic polymeric membrane containing a hydrocarbon chain with a reactive group is formed on the measuring electrode (the 'immunoelectrode') in a thickness of about 10 to 50 microns, with a thickness of about 20 to 40 microns being particularly preferred. The membrane preferably does not exceed $100\mu$, nor is less than $5\mu$ in thickness. A protein or other appropriate compound of an immunochemical pair is immobilised in the membrane. The measuring electrode is used in conjunction with a reference electrode. The two electrodes are immersed in a mixture, typically a solution which contains a protein or other compound of the type sought to be identified. The measuring electrode and the reference electrode are electrically connected to a meter sensitive to very slight changes in electrical potential. As the particular protein is captured by the measuring electrode, the electrical potential at the polymer-solution interface changes. The slight change is detected by the meter, which has a high impedence in electrode circuitry, thus indicating the presence of the compound. By calibration, the meter may be used to determine quantitatively the amount of compound present in the solution.

The reference electrode may be of any of a wide range of convenient electrode materials many of which are known, although we have found it advantageous to employ as the reference electrode a second immunoelectrode, substantially identical with the measuring electrode except that the specific reactive sites are blocked with a suitably reactive blocking agent so that the reference electrode is no longer responsive to the particular material being tested for. It does, however respond to non-selective adsorption of other molecules in the test solution as does the measuring electrode, so that the effect of non-selective adsorption, where it occurs, may be compensated for; measurement of the potential of an active measuring immunoelectrode against the potential of an identical (reference) immunoelectrode with blocked binding sites can effectively eliminate the effect of non-specific interactions.

Compositions and particularly membranes according to the invention also find application as preparative or reaction aids, facilitating immobilisation of one or more reactants with the potential of reversible immobilisation for example by changing the polarity of the membrane by passing an electric current through it.

The invention is illustrated by the following example.

EXAMPLE

Preparation of methyl dodecyl imido ester 5.0 ml of dodecyl nitrile was dissolved in 5.0 ml of dry methanol and 50 ml of dry ether contained in a flask fitted with a condenser. The mixture was cooled in an ice-bath and dry HCl slowly bubbled through it for 1 hour. A drying tube was attached at the end of the condenser. The flask was then sealed and held for 24 hours at 0° C. Ether was then evaporated under vacuum (at 30° C.) until the ester crystallised as white solid. This was washed with dry ether three times. The dry solid was stored at +4° C. in a desiccator.

Preparation of Membrane

PVC film is pre-swelled in dry toluene for 5 minutes and then placed in mixture of methanol:toluene:petrol ether (30–60) (1:2:1) containing 3% of the imidoester. After the three hour period the film is placed in a vacuum desiccator for 1 hour after which time the excess of the imidoester is washed off with dry methanol. Any traces of the swelling mixture are then removed in a vacuum drying pistol at room temperature for 12 hours. The film is then left in the solution containing 5% of protein to be immobilised (pH 8.4) for 48 hours at room temperature and at the end of this period washed in buffer/physiological saline solution.

This procedure can be used as a general procedure for immobilisation of proteins on hydrophobic polymers.

What I claim is:

1. In a composition comprising a hydrophobic organic polymeric substrate having essentially hydrocarbon chains absorbed onto the surface thereof, said hydrocarbon chains having a group reactive with a protein attached thereto, the improvement which comprises as a protein reactive group an ionic protein bonding linkage to said hydrocarbon chains, said ionic linkage being derived from an imido ester of the formula

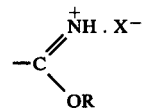

where R is an alkyl group and $X^-$ is HCl or HBr.

2. A composition according to claim 1 in which the linkage is derived from a methyl dodecyl imido ester.

3. A composition according to claim 1 in which the composition is in the form of a membrane.

4. A composition according to claim 1 in association with an electrode responsive to a change in the electrical charge of the composition.

5. A composition according to claim 1 in which the specific protein reactive group is an antibody or an antigen.

6. Apparatus comprising a composition according to claim 1 and means for detecting a change in the electrical potential associated with the said composition when it contacts a chemical substance reactive with the specific protein reactive group attached to said composition.

7. A method of detecting the presence of a chemical substance which comprises contacting the chemical substance with an electrode in association with the composition of claim 1, said composition being specifically reactive with the chemical substance and said electrode being responsive to a change in the electrical charge in said composition, and detecting any resultant change in the said electrical charge.

* * * * *